United States Patent [19]
Lin et al.

[11] Patent Number: 6,066,294
[45] Date of Patent: May 23, 2000

[54] MULTI-COMPARTMENT STERILIZATION SYSTEM

[75] Inventors: Szu-Min Lin, Laguna Hills; Paul Taylor Jacobs, Trabuco Canyon, both of Calif.

[73] Assignee: Ethicon, Inc., New Brunswick, N.J.

[21] Appl. No.: 08/915,922

[22] Filed: Aug. 21, 1997

[51] Int. Cl.⁷ .................................... A61L 2/16
[52] U.S. Cl. .................. 422/28; 422/33; 422/300; 134/170; 134/183
[58] Field of Search .................. 422/28, 33, 292, 422/297, 300, 305; 134/84, 88, 89, 92, 170, 183

[56] References Cited

U.S. PATENT DOCUMENTS

| | | |
|---|---|---|
| 4,744,951 | 5/1988 | Cummings et al. . |
| 4,797,255 | 1/1989 | Hatanaka et al. . |
| 4,863,688 | 9/1989 | Schmidt et al. . |
| 4,937,046 | 6/1990 | Andersen et al. . |
| 4,943,414 | 7/1990 | Jacobs et al. . |
| 5,118,471 | 6/1992 | Andersen et al. . |
| 5,122,344 | 6/1992 | Schmoegner . |
| 5,227,132 | 7/1993 | Andersen et al. . |
| 5,266,275 | 11/1993 | Faddis . |
| 5,445,792 | 8/1995 | Rickloff et al. . |
| 5,508,009 | 4/1996 | Rickloff et al. . |
| 5,534,222 | 7/1996 | Kelbrick et al. .................. 422/28 X |
| 5,633,424 | 5/1997 | Graves et al. . |
| 5,641,464 | 6/1997 | Briggs, III et al. .................. 422/300 |
| 5,667,753 | 9/1997 | Jacobs et al. .................. 422/29 |
| 5,711,921 | 1/1998 | Langford .................. 422/300 X |
| 5,846,484 | 12/1998 | Scarborough et al. .................. 422/292 X |

*Primary Examiner*—Elizabeth McKane
*Attorney, Agent, or Firm*—Knobbe, Martens, Olson & Bear, LLP

[57] ABSTRACT

An apparatus for the sterilization of a medical device includes a multi-chambered compartment having at least a first and a second rigid chamber therein. Each of the first and second chambers is adapted to independently serve as a sterilization chamber and can be operated independently. The apparatus also has a removable interface between the first and second chamber. The interface can have an opening for receiving a lumen device in such a way that the first and second chamber is put in fluid communication through the lumen. A source of sterilant is also included in the apparatus. This source is adapted to provide the sterilant in the first and/or second chamber. Containers sealed with gas-permeable, but microorganism-impermeable membrane can be used in the apparatus so that the sterility of the devices in the container is kept after the completion of a sterilization cycle.

52 Claims, 8 Drawing Sheets

MULTI-COMPARTMENT STERILIZATION SYSTEM

BACKGROUND OF THE INVENTION

1. Field of the Invention

The invention relates to systems used for chemical sterilization of medical devices, and more particularly, to systems having multiple chambers used for chemical sterilization of medical devices.

2. Description of the Related Art

Medical instruments have traditionally been sterilized using either heat, such as is provided by steam, or a chemical, in the gas or vapor state. Sterilization using hydrogen peroxide vapor has been shown to have some advantages over other chemical sterilization processes.

The combination of hydrogen peroxide with a plasma provides certain additional advantages, as disclosed in U.S. Pat. No. 4,643,876, issued Feb. 17, 1987 to Jacobs et al. U.S. Pat. No. 4,756,882, issued Jul. 12, 1988 also to Jacobs et al. discloses the use of hydrogen peroxide vapor, generated from an aqueous solution of hydrogen peroxide, as a precursor of the reactive species generated by a plasma generator. The combination of hydrogen peroxide vapor diffusing into close proximity with the article to be sterilized and plasma acts to sterilize the articles and remove residual hydrogen peroxide. However, effective sterilization of articles having long narrow lumens are very difficult to achieve, since the methods are dependent upon diffusion of the sterilant vapor into close proximity with the article before sterilization can be achieved. Thus, these methods have been found to require high concentration of sterilant, extended exposure time and/or elevated temperatures when used on long, narrow lumens. For example, lumens longer than 27 cm and/or having an internal diameter of less than 0.3 cm have been particularly difficult to sterilize. The sterilization of articles containing long narrow lumens therefore presents a special challenge.

U.S. Pat. No. 4,744,951 to Cummings et al. discloses a two-chambered system which provides hydrogen peroxide in vapor form for use in sterilization processes. The sterilant is initially vaporized in one chamber and then applied to the object to be sanitized in another single sterilizing chamber, thereby producing a concentrated hydrogen peroxide vapor which is relatively more effective. The sterilization processes are designed for furnishing concentrated hydrogen peroxide vapor to interior surfaces of articles having a tortuous or a narrow path. However, the sterilization processes are ineffective at rapidly sterilizing lumened devices, since they depend on the diffusion of the hydrogen peroxide vapor into the lumen to effect sterilization.

U.S. Pat. No. 4,797,255 to Hatanaka et al. discloses a two-chambered sterilization and filling system consisting of a single sterilization chamber adjacent to a germ-free chamber utilized for drying and filling sterilized containers.

U.S. Pat. No. 4,863,688 to Schmidt et al. discloses a sterilization system consisting of a liquid hydrogen peroxide vaporization chamber and an enclosure for sterilization. The enclosure additionally may hold containers wherein the hydrogen peroxide sterilant vapor does not contact the interior of the containers. This system is designed for controlling the exposure to the hydrogen peroxide vapor. The system is not designed for sterilizing a lumen device.

U.S. Pat. No. 4,952,370 to Cummings et al. discloses a sterilization process wherein aqueous hydrogen peroxide vapor is first condensed on the article to be sterilized, and then a source of vacuum is applied to the sterilization chamber to evaporate the water and hydrogen peroxide from the article. This method is suitable to sterilize surfaces, however, it is ineffective at rapidly sterilizing lumened devices, since it too depends on the diffusion of the hydrogen peroxide vapor into the lumen to effect sterilization.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized.

U.S. Pat. Nos. 4,937,046, 5,118,471 and 5,227,132 to Anderson et al. each disclose a sterilization system which uses ethylene oxide gas for sanitation purposes. The gas is initially in a small first enclosure and thereafter slowly permeates into a second enclosure where the objects to be sterilized are located. A medium is then introduced into the second enclosure to flush out the sterilizing gas into a third enclosure containing the second enclosure. An exhaust system then exhausts the sterilant gas and air from the third enclosure. These systems also have the disadvantage of relying on the diffusion of the sterilant vapor to effect sterilization and hence are not suitable for rapidly sterilizing lumened devices.

U.S. Pat. No. 5,122,344 to Schmoegner discloses a chemical sterilizer system for sterilizing items by vaporizing a liquid chemical sterilant in a sterilizing chamber. Pre-evacuation of the sterilizer chamber enhances the sterilizing activity. Sterilant is injected into the sterilizer chamber from a second prefilled shot chamber. This system also relies upon diffusion of sterilant vapor to effect sterilization and is also not suitable for rapidly sterilizing lumened devices.

U.S. Pat. No. 5,266,275 to Faddis discloses a sterilization system for disinfecting instruments. The sterilization system contains a primary sterilization chamber and a secondary safety chamber. The secondary safety chamber provides for sensing and venting to a destruction chamber any sterilization agent that is released from the primary sterilization chamber. This system, as in other systems, also relies upon diffusion of sterilant vapor to effect sterilization and is also not suitable for rapidly sterilizing lumened devices.

In U.S. Pat. Nos. 5,492,672 and 5,556,607 to Childers et al, there is disclosed a process and apparatus respectively for sterilizing narrow lumens. This process and apparatus uses a multicomponent sterilant vapor and requires successive alternating periods of flow of sterilant vapor and discontinuance of such flow. A complex apparatus is used to accomplish the method. Additionally, the process and apparatus of '672 and '607 require maintaining the pressure in the sterilization chamber at a predetermined subatmospheric pressure.

In U.S. Pat. No. 5,527,508 to Childers et al., a method of enhancing the penetration of low vapor pressure chemical vapor sterilants into the apertures and openings of complex objects is disclosed. The method repeatedly introduces air or an inert gas into the closed sterilization chamber in an amount effective to raise the pressure to a subatmospheric pressure to drive the diffused sterilant vapor further into the article to achieve sterilization. The '508, '672 and '607

Childers inventions are similar in that all three require repeated pulsations of sterilant vapor flow and maintenance of the sterilization chamber pressure at a predetermined subatmospheric pressure.

In U.S. Pat. No. 5,534,221 to Hillebrenner et al., a device and method for sterilizing and storing an endoscope or other lumened medical device is disclosed. The device includes a sealable cassette in which the endoscope or other medical device is placed. The cassette has an input port for receiving a sterilizing agent through a connector, an output port for expelling the sterilizing agent when a vacuum is applied thereto through a connector, and check valves in the input and output ports to open the ports when the connectors are coupled to the ports and to seal the ports when the connectors are removed from the ports such that after the endoscope has been sterilized, it remains sterilized within the cassette until the cassette is opened. The method of the '221 invention involves placing the medical device inside the cassette and coupling the device to either the input or output port of the cassette. The cassette is then placed in an outer oven-like container or warming chamber where the temperature is properly maintained. Connections are made to open the input and output ports on the cassette such that the sterilizing agent may be introduced through a first port to bathe the outside of the medical instrument or other object, such as an endoscope while one end of the hollow object, such as the endoscope, is coupled to the output port where a vacuum is supplied external to the cassette to pull the sterilization agent into the cassette and through the interior passageways of the endoscope. When the sterilization process is completed, the warming chamber is opened and the sterilizing cassette is simply removed from the chamber with the input and output ports being uncoupled from their respective sources. A tight seal is maintained and the object remains in the sterilized interior of the cassette until the cassette is opened or the device is to be used. Thus, the '221 invention is concerned with providing a means whereby a sterilized medical device can be retained within a cassette in which it was sterilized until ready for use, thus avoiding any contamination by exposure to the atmosphere or handling before use. Additionally, in some cases of the '221 invention, wherein the lumen of the device to be sterilized is connected to the output port, particularly wherein the devices have long, narrow lumens, the time to expel the sterilizing agent through the lumen and out of the cassette may be undesirably long. Also, in cases wherein the lumen device is very flexible, lumen collapse may occur, either slowing or preventing vapor exit or causing lumen damage.

U.S. Patents Nos. 5,445,792 and 5,508,009 to Rickloff et al. each disclose a sterilization system essentially equivalent to the system disclosed in Hillebrenner '221.

U.S. Pat. No. 5,443,801 to Langford teaches a transportable cleaning/sterilizing apparatus and a method for inside-outside sterilization of medical/dental instruments. The apparatus avoids the use of heat, pressure, severe agitation, or corrosive chemicals which might damage delicate equipment. This invention uses ozone gas or solution as sterilant. It does not involve the use of sterilant vapor or vaporizing a sterilant solution into vapor, and is not suitable for operations under vacuum because flexible bags or containers are used.

In consideration of the foregoing, no simple, safe, effective method of sterilizing smaller lumens exists in the prior art. Thus, there remains a need for a simple and effective method of vapor sterilization of articles with both long, narrow lumens as well as shorter, wider lumens. Furthermore, there also remains a need for a simple and effective sterilization system with independently operable chambers.

SUMMARY OF THE INVENTION

One aspect of the present invention relates to a multi-compartment sterilization apparatus for the sterilization of a medical device. The apparatus comprises a multi-chambered compartment having at least a first rigid chamber and a second rigid chamber, an openable and closeable interface between the first and second chamber, and a source of sterilant adapted to provide the sterilant in the first and/or second chamber, wherein each of the first and second chambers can be operated independently as a sterilization chamber. The apparatus may further comprises a flow path between the first and second chamber. Preferably, the interface is removable. In one embodiment, the interface is openable and closeable by being removable. The apparatus can further comprise a gas and sterilant vapor-permeable, microorganism-impermeable container in either the first chamber or the second chamber, and the device to be sterilized is placed in the container. The container serves to maintain the sterility of the device following sterilization. The device to be sterilized can be placed in either the first chamber or the second chamber. In one embodiment, each of the first and second chamber provides a diffusion restricted environment. In another embodiment, the first chamber and the second chamber have a first and a second sealable door, respectively, and the second sealable door is smaller than the first door and located in the first door. In one embodiment, the interface has at least one opening, wherein the device to be sterilized comprises a lumen, and the lumen of the device is placed through the opening such that the lumen is located partly in each of the first and second chambers. The opening can form a gas-tight seal around the lumen or form a loose-fitting seal around the lumen allowing sterilant to flow outside of the lumen through the opening, or form a tight-fitting seal around the lumen with the seal comprising a gas and/or liquid permeable material. An opening without a lumen can be further provided in the interface. In one embodiment, the flow path is inside the multi-chambered compartment. Preferably, the flow path allows flow in both directions. The flow path is preferably through a lumen device. In another embodiment, the flow path is outside the multi-chambered compartment which allows flow in both directions. The apparatus may further comprise a second flow path in addition to the first flow path. In one embodiment, the second flow path is outside the multi-chambered compartment and the first flow path is in the interface. In another embodiment, the first flow path is inside the multi-chambered compartment and the second flow path is outside the multi-chambered compartment. The source of sterilant is preferably selected from the group consisting of an injector, a liquid flow-through device, a liquid or solid reservoir or aerosol spray device. The source of sterilant is preferably placed in a location selected from the group consisting of: the first chamber; the second chamber; a container placed in the sterilization multi-chambered compartment; an enclosure placed outside of the sterilization multi-chambered compartment. In one embodiment, the enclosure is connected to one of the first and second chambers, or to both of the first and second chamber. In another embodiment, the enclosure is connected to the container. The source of sterilant can be liquid reservoir. The sterilant may comprise a liquid, a solid or condensed vapor. The liquid sterilant preferably comprises hydrogen peroxide or peracetic acid. The sterilant can be a solid hydrogen peroxide complex. The hydrogen peroxide complex preferably comprises a urea peroxide complex or sodium pyrophosphate peroxide complex or like complex. In one embodiment, the sterilant is a condensed vapor which comprises hydrogen peroxide or peracetic acid vapor. The flow system may comprise a vacuum pump for applying vacuum, a pump for circulating sterilant, or heat-induced pressurization. The apparatus may further comprise at least one additional interface. The apparatus can further comprise a heater to vaporize the sterilant. The apparatus can further comprise a plasma generator for exposing the device to be sterilized to a plasma. The plasma generator can be located in a separate container and the apparatus further comprises a flow system to flow said plasma into the multi-chambered compartment. In one embodiment, the opening in the interface is provided with an iris diaphragm. In another embodiment, the opening is defined by two plates. The plates have compressible material at edges or on surfaces adjacent the opening, and at least one of the plates is movable. In still another embodiment, the opening is equipped with inflatable material so that when the inflatable material is inflated the opening is reduced to hold and seal a device to be sterilized.

Another aspect of the present invention relates to a method for sterilizing a medical device. The method for sterilizing an interior and exterior of a lumen device comprises: a. placing the device in a multi-chambered compartment having a first chamber, a second chamber, and an interface with at least one opening, such that the lumen is partly in the first chamber and partly in the second chamber across the interface; b. introducing a sterilant from a source of sterilant in the multi-chambered compartment; and c. creating a flow of sterilant between the first chamber and the second chamber through the lumen. Prior to the placing step, the device can be placed in a sterilant vapor-permeable and microorganism-impermeable container, the container maintains the sterility of the device following sterilization. A non-lumen device can be sterilized in either of the first or second chambers. The placing step may further comprise the steps of: removing the interface; replacing the interface with a different interface to accommodate different lumen. In one embodiment, either or both of the first and second chambers is a diffusion restricted environment. The sizes of the first and second chambers can be different. The method may additionally comprise placing the lumen in the opening such that the lumen is located partly in each of the first and second chambers. The opening may form a gas-tight seal around the lumen, or form a loose-fitting seal around the lumen allowing sterilant to flow outside of the lumen through the opening, or form a tight-fitting seal around the lumen with the seal comprising a gas and/or liquid permeable material. The interface may have an opening without a lumen. The flow path can be inside said multi-chambered compartment which allows flow in both directions. In addition to the first flow path, the method may further comprise flowing sterilant through a second flow path. In one embodiment, the first flow path is inside the multi-chambered compartment and the second flow path is outside the multi-chambered compartment. The source of sterilant can be placed in a location selected from the group consisting of: the first chamber; the second chamber; a container wherein the container is placed in the sterilization multi-chambered compartment; an enclosure placed outside of the multi-chambered compartment, wherein the enclosure can be connected to one of the first and second chambers, or to both of the first and second chamber, or to the container. In one embodiment, the source of sterilant is a liquid reservoir. The sterilant may comprise a liquid, a solid or condensed vapor. In one embodiment, the sterilant is a liquid which comprises hydrogen peroxide or peracetic acid. In another embodiment, sterilant is a solid hydrogen peroxide complex. The solid may comprise a urea peroxide complex or sodium pyrophosphate peroxide complex. In another embodiment, the sterilant is a condensed vapor, the method further comprising condensing sterilant vapor. Preferably, the condensed vapor is of hydrogen peroxide or peracetic acid vapor. A flow system comprising a vacuum pump, a pump for circulating sterilant or heat-induced pressurization can be used to accomplish the flowing step. The method may further comprise the step of exposing the device to a plasma. The plasma can be generated in a separate container and the method further comprises the step of flowing the plasma from the container into the first or second sterilization chamber. The method may further comprise warming the device to be sterilized prior to step (b). The device to be warmed can be warmed with an applied electric field. Preferably, the device is warmed at pressure below atmospheric pressure. The steps (b) and (c) can be repeated one or more times. The step (a) may further comprises the steps of: opening the opening in the interface; inserting the device through the opening such that the device is partly in the first chamber and partly in the second chamber; and then closing the opening such that a seal is formed around the device. The step (a) may also comprises placing the device through the opening equipped with an iris diaphragm which can seal around the device; or placing the device through the opening defined by two plates, the plates have compressible material at edges or on surfaces of the plate adjacent the opening, at least one of the plates is movable, so that the plates can be brought toward each other to hold and seal around the device; or placing the device through the opening equipped with inflatable material, so that when the inflatable material is inflated the opening is reduced to hold and seal around the device. In one embodiment, step (a) comprises placing the device through a opening equipped with expendable material, and expanding the expendable material to seal around the device; or placing the device through a opening equipped with compressible material, and compressing the compressible material to seal around the device. In one preferred embodiment, the lumen device to be sterilized is an endoscope. In another embodiment, the lumen has at least two ends and the lumen crosses the interface through the opening in between the ends.

Another aspect of the present invention relates to a method for sterilizing a medical device. The method comprises the steps of: a. placing the device in a multi-chambered compartment having a first rigid chamber, a second rigid chamber, and a removable interface between the first and second chambers; b. adjusting the interface so that a device too big to fit into the first or second chamber can be sterilized in a bigger chamber formed by the first and second chamber; and c. introducing a sterilant from a source of sterilant in the multi-chambered compartment. Prior to the placing step, the device is placed in a sterilant vapor-permeable and microorganism-impermeable container, the container maintains the sterility of the device following sterilization.

DETAILED DESCRIPTION OF THE PREFERRED EMBODIMENT

The multi-compartment sterilization apparatus of the present invention is suitable for the sterilization of both non-lumen and lumen devices.

According to one aspect of the present invention, the multi-compartment sterilization apparatus comprises at least two chambers separated by a sealable and removable interface. Each of the chambers can be operated independently and serve as a sterilization chamber. In a sterilization process using the apparatus of the present invention, the interface can be adjusted for different situations. For example, if the device to be sterilized is too big to fit into neither one of the two chambers, the interface can be removed so that more space will be available to accommodate the device. If the device is not so big, it can be sterilized in one of the two chambers while other devices can be prepared for sterilization in the other chamber.

According to another aspect of the present invention, the multicompartment sterilization apparatus comprises a sterilization system with a multi-chambered compartment having at least a first rigid chamber and a second rigid chamber, an openable and closeable interface between the first and second chamber, a flow path between the first and second chamber, and a source of sterilant adapted to provide the sterilant in the first and/or second chamber. The flow path can be a lumen of the device to be sterilized, so that sterilant can flow directly through the lumen to sterilize the interior of the lumen device. Different sterilization methods and technologies can be used in corporation with the sterilization system of the present invention. Several embodiments of those methods are described below:

Method to Deliver a Predetermined Amount of Liquid Sterilant

Conventional sterilants can be used in the present invention. Numerous sterilants are available in the art, such as formaldehyde, ethylene oxide, hydrogen peroxide solution and hydrogen peroxide vapor. Although any of those sterilants can be used in the sterilization apparatus of the present invention, the use of hydrogen peroxide solution and hydrogen peroxide vapor has been shown to have some advantages over other chemical sterilization processes. Therefore, it is preferred to use hydrogen peroxide solution and hydrogen peroxide vapor as sterilant in the present invention. In a sterilization process using hydrogen peroxide solution as sterilant, the sterilant can be applied in several different ways. For example, a hydrogen peroxide solution can be first vaporized under vacuum and/or heat in a vacuum chamber, and the device to be sterilized is then exposed to the hydrogen peroxide vapor. Accordingly, in one embodiment of the present invention, an important parameter of the process needed to achieve satisfactory sterilization is the amount of liquid hydrogen peroxide entering into the chamber to be vaporized. Thus, it is important that the liquid hydrogen peroxide be delivered to the chamber in measured quantities.

A sterilization apparatus able to deliver a predetermined amount of liquid sterilant can be incorporated into the sterilization system of the present invention. Thus, the sterilization chamber may have a bottom wall with at least one well which defines a known volume. The well is positioned so that when a liquid sterilant is introduced onto the bottom surface, a known volume of the liquid sterilant fills the well and when the liquid sterilant is drained from the surface, the known volume of liquid sterilant remains in the well so that a subsequent sterilization process can be performed on the device positioned on the bottom surface with the known volume of liquid sterilant positioned within the bottom surface. The apparatus may also include a heat source and/or a vacuum source for vaporizing the liquid sterilant in the well, and can optionally include a source of plasma. The bottom surface preferably has at least one perforation for draining the liquid sterilant from the bottom surface. The well formed in the bottom surface can be curved, flat or angled. Thus, the well can be an inwardly extending hemispherical projection. The well can also be formed in the bottom surface as an inwardly extending rectangular projection having rounded ends. The well formed in the bottom surface can also be a rectangular box having side walls, defining an opening. Where perforations are provided, they can be disposed adjacent the well, and can be roughly spherical in shape. The upwardly extending projection can include a perforation thereon, which can be on top of the projection or on a side of the projection. The bottom surface can be a sloped surface, a convex or concave surface or a V-shaped surface. The bottom surface can be of a variety of materials including stainless steels, aluminum, aluminum alloys, liquid crystal polymers, polyesters, polyolefin polymers or fluorinated polyolefins. If the bottom surface is comprised of a composite material, the composite material can include a filler of high thermal conductivity. Examples of composite materials include a metalfilled polymer, a ceramic-filled polymer and a glass-filled polymer. Those materials are also suitable for the side walls and doors of the sterilization chamber.

Method Based on Diffusion Restricted Environments

A method of hydrogen peroxide vapor sterilization of diffusion-restricted environments can also be used in corporation with the present invention. In this embodiment of the present invention, the devices (lumen or non-lumen) to be sterilized are pretreated with a hydrogen peroxide solution, and then exposed to pressures less than the vapor pressure of sterilant. The inside of lumens is sterilized by taking advantage of the diffusion-restricted environments within the lumens.

As used herein, a "diffusion-restricted" area refers to any one or more of the following properties: (1) the ability of the area of an article placed within the sterilization system of the present invention to retain 0.17 mg/L or more hydrogen peroxide solution after one hour at 40° C. and 10 torr; (2)

having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the hydrogen peroxide solution placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

In this embodiment of the present invention, a method for sterilizing an interior of a device with a diffusion restricted area, such as a device having a lumen, is used in corporation with the sterilization system. The method includes the steps of contacting the interior of the device with a liquid solution comprising hydrogen peroxide, and exposing the device to negative pressure for a time period sufficient to effect complete sterilization. In one embodiment, the liquid solution is peracetic acid. If the exposing step is conducted for 1 hour at 40° C. and 10 torr, the diffusion restricted area preferably retains 0.17 mg/L or more hydrogen peroxide, or retains 17% or more of the hydrogen peroxide placed therein after the exposing step. In certain preferred embodiments, the diffusion-restricted area has the same or more diffusion restriction than provided by a lumen 27 cm in length and an internal diameter of 3 mm, or has the same or more diffusion restriction than provided by a lumen having a ratio of length to internal diameter greater than 50. The solution is preferably at a concentration of less than 25% by weight. The contacting step can be performed by delivery via a method such as injection, static soak, liquid flow-through or aerosol spray. In a preferred embodiment, the diffusion-restricted area is a lumen at least 27 cm in length and having an internal diameter of no more than 3 mm, more preferably having an internal diameter of no more than 1 mm. The exposing step is preferably performed for 60 minutes or less, and is preferably performed at a pressure less than the vapor pressure of hydrogen peroxide. Thus, the preferred pressure range under conditions of the present invention is between 0 and 100 torr. In one particularly preferred embodiment, the pressure is approximately 10 torr and the exposing step is conducted at a temperature of approximately 23° C. to approximately 28° C. The exposing step can include the step of heating the article, such as by heating the chamber in which the exposing step occurs. The chamber can be heated to about 40° C. to about 45° C. Alternatively, the solution can be heated, such as to a temperature of about 40° C. to about 45° C. Optionally, the step of exposing the device to a plasma can be conducted during the step of exposing the device to negative pressure. In one embodiment employing exposure to plasma, the method is performed within a first chamber and the plasma is generated in a second, separate chamber. This embodiment further comprises the step of flowing the plasma into the first chamber. Advantageously, the contacting and/or exposing steps of the method can be repeated one or more times.

Sterilization Methods in Non-diffusion Restricted Environments

The present invention can also be used to sterilize devices with lumens without relying on a diffusion-restricted environment.

It has been discovered by the inventors that similar sterilization results to those created in diffusion-restricted environments can be created through controlling the evacuation rate of the chamber in which articles to be sterilized are placed. Thus, in one embodiment of the present invention, a method for sterilizing a device can be used in corporation with the sterilization system of the present invention. The method comprises the steps of contacting the device with liquid sterilant outside or inside a sterilization chamber at a first pressure; placing the device in the chamber before or after the contacting step; and decreasing the pressure of the chamber to a second pressure below the vapor pressure of the liquid sterilant in which at least a portion of the decrease in pressure below about the vapor pressure of the liquid sterilant occurs at a pumpdown rate of less than 0.8 liters per second, calculated based on the time required to evacuate the chamber from atmospheric pressure to 20 torr when the chamber is empty and dry, i.e. when the chamber has neither articles to be sterilized nor a visible quantity of liquid within it. According to one aspect of this preferred embodiment, at least the decrease in pressure below about two times the vapor pressure of the liquid sterilant occurs at a pumpdown rate of less than 0.8 liters per second. According to another aspect of this embodiment, the decrease in pressure below about four times the vapor pressure of the liquid sterilant occurs at a pumpdown rate of less than 0.8 liters per second. Preferably, the pumpdown rate is 0.6 liters per second or less; more preferably, 0.4 liters per second or less; and most preferably, 0.2 liters per second or less. Advantageously, the first pressure is atmospheric pressure. Preferably, the liquid sterilant is hydrogen peroxide. In another aspect, the device is a medical instrument having a lumen.

The present invention can also use a method for sterilizing a device comprising the steps of (a) contacting the device with liquid sterilant outside or inside a sterilization chamber at a first pressure; (b) placing the device in the chamber before or after the contacting step; (c) pumping down the chamber to a second pressure which is lower than the first pressure at a first rate; and (d) pumping down the chamber to a third pressure which is lower than the second pressure, wherein at least a portion of the pumping down to the third pressure is at a second rate which is slower than the first rate. The pumpdown rate either above and/or below the second pressure can be constant or variable. In certain embodiments, the pumpdown rate either above and/or below the second pressure is reduced in stepwise fashion. Preferably, the second pressure is greater than or equal to about the vapor pressure of the liquid sterilant; more preferably, the second pressure is greater than or equal to about two times the vapor pressure of the liquid sterilant; most preferably, the second pressure is greater than or equal to about four times the vapor pressure of the liquid sterilant. Advantageously, the pumpdown rate in step (d) is 0.8 liters/sec or less; more advantageously 0.6 liters/sec or less; even more advantageously 0.4 liters/sec or less; and most advantageously 0.2 liters/sec or less, calculated based on the time required to evacuate the chamber from atmospheric pressure to 20 torr under empty and dry conditions. Preferably, the liquid sterilant is hydrogen peroxide. In another aspect of this embodiment, the device is a medical instrument having a lumen. Preferably, the pumping down of step (c) reduces the pressure to less than about three times, more preferably to less than about two times, the vapor pressure of the liquid sterilant.

Another suitable method includes contacting the article with liquid sterilant either inside or outside of the sterilization chamber, placing the device in the chamber either before or after the contacting step, and reducing the pressure of the chamber while regulating the pumpdown rate so as to control the evaporation rate of sterilant in said chamber. In any of the methods described above, the contacting step may comprise application of liquid or condensed vapor. These methods described above may additionally comprise further evacuating the chamber to remove residual sterilant. Further, these methods described above may additionally comprise exposing the device to plasma to remove residual sterilant or enhance sterilization efficacy. The contacting step in these methods can be either by direct or indirect contacting. As stated hereinbelow, indirect contacting involves introducing sterilant into the chamber without directly contacting the article to be sterilized.

In another embodiment, a two step pump down sterilization process can be used in connection with the sterilization system of the present invention. The method comprises the steps of: contacting a device with liquid sterilant outside or inside a sterilization chamber; placing the device in the chamber before or after the contacting step; bringing the pressure of the chamber to a first pressure range at which liquid sterilant is vaporized from the non-diffusion restricted area to sterilize the non-diffusion restricted area; bringing the pressure of the chamber to a second pressure range at which the liquid sterilant is vaporized from the diffusion restricted area to sterilize the diffusion restricted area, wherein the minimum pressure in the second pressure range is lower than the maximum pressure in the first pressure range.

Preferably, the first pressure range is 20 to 760 torr; more preferably, the first pressure range is 20 to 80 torr; most preferably, the first pressure range is 40–50 torr. Advantageously, the second pressure range is 1–30 torr; more advantageously, the second pressure range is 5–10 torr. In one aspect of this preferred embodiment, the device includes a diffusion-restricted environment. Preferably, the device is a medical instrument with a lumen having an interior and an exterior surface. Advantageously, the sterilant is hydrogen peroxide. According to another aspect of this preferred embodiment, the chamber is at a set temperature and wherein the first pressure is greater than the vapor pressure of the sterilant at the set temperature. Preferably, the pressure of the chamber is maintained constant at the first pressure for a time period sufficient to sterilize the non-diffusion restricted area. Advantageously, the pressure of the chamber is maintained constant at the second pressure for a time period sufficient to sterilize the diffusion restricted area. The pressure of the chamber may be permitted to increase after reaching the first or second pressure range as a result of vaporization of the sterilant within said chamber. Alternatively, the pressure of the chamber is permitted to decrease after reaching the first or second pressure through pumping of said chamber at a rate slower than used to decrease the pressure between said first and second pressure ranges. Preferably, the contacting step is with liquid or condensed vapor. The method can also include the steps of bringing the pressure to a third pressure lower than the second pressure to remove residual sterilant and/or exposing the device to plasma to remove residual sterilant or enhance sterilization efficacy.

Method Involving Direct Flow Through a Lumen of Devices to Be Sterilized

According to the present invention, a sterilization apparatus is provided which can more efficiently sterilize devices with long narrow lumens by flowing a sterilant, either in liquid phase or in vapor phase, directly through the lumens of lumen devices to be sterilized.

The flow of a sterilant (solution or vapor) through a lumen of a medical device is realized by a pressure drop between two ends of the lumen. The pressure drop can be generated by applying either a vacuum or a high pressure at one end. By generating a forced flow through a pressure differential other than relying on diffusion, the sterilization rate is significantly increased and less time is needed for a sterilization cycle.

It is clear from the above discussion that the two ends of the lumen need to be exposed to a pressure differential. This is achieved in the present invention by placing a sealable interface between the two chambers. An opening is provided in the interface and the lumen device to be sterilized is placed through the opening in such a way that the lumen serves as a flow path between the two chambers.

The opening can be constructed in several ways. One way to achieve this is with a camera shutter approach employing an iris diaphragm, such as a precision iris diaphragm from Edmund Scientific. An optional spring can be used to secure the closure of the shutter. Another way to achieve an acceptable opening is to employ two plates, wherein the area between the two plates has a compressible material, such as a rubber material. The lumen device can be placed between the two plates and the two plates moved together to form a gas and vapor impermeable seal around the lumen device. Optionally, a porous material like a sponge or air permeable material may be utilized for the compressible material. In this case some sterilant can flow between the compressible material and the lumen device. However, most the sterilant flows through the lumen device. Yet another acceptable interface is a hole or horizontal opening for one or more lumen devices, said hole or opening being a gas or liquid inflatable so that by inflating the inflatable material on the hole or opening the lumen devices are held and sealed. Still another option is to place a compressible material on top of an inflatable material so as to facilitate the sealing around the lumen device.

The closing and opening movement of the opening such as the plate and the iris diaphragm can be controlled mechanically or electronically with any conventional mechanism.

It is sealed to a different degree between the opening and the lumen device depending on the desired purpose. For example, the opening can form a gas-tight seal around the lumen device so that nothing can flow outside of the lumen device through the opening; or form a loose-fitting seal around the lumen device allowing sterilant to flow outside of the lumen device through the opening so that the exterior of the lumen device adjacent the opening can be sterilized; or form a tight-fitting with a porous material, such as a gas and/or liquid permeable membrane around the lumen device so that gas and sterilant can pass and, in the meantime, the porous material helps to hold the lumen device. The interface can be made openable, closeable, and removable. A flow path between different chambers can be also provided outside the sterilization system.

In order to promote sterilization efficiency, all the sterilization apparatus of the present invention can be further equipped with a heater, vacuum, and/or a plasma.

Figure 1:
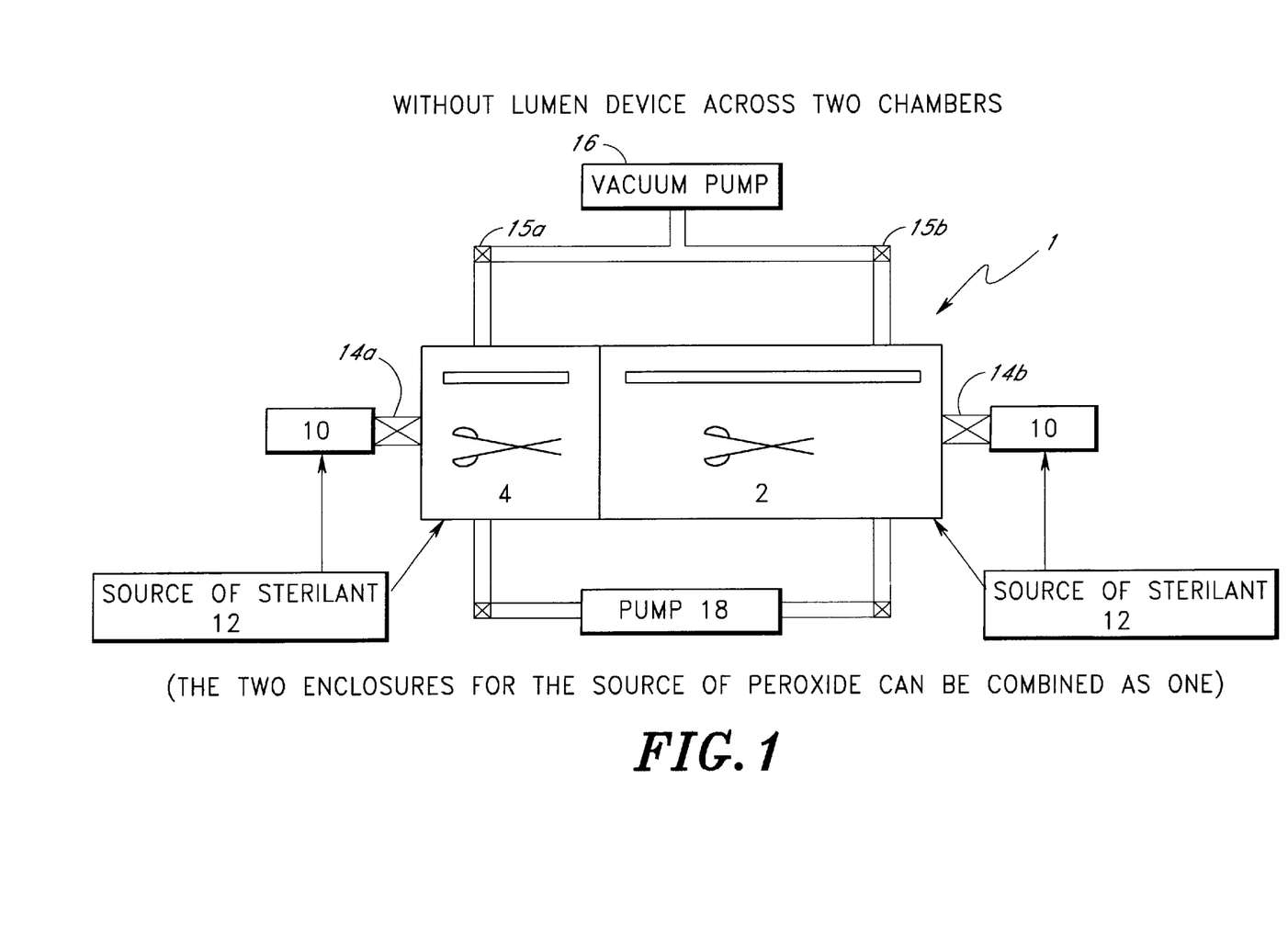
FIG. 1 is a schematic diagram of an embodiment of the apparatus of the present invention showing two chambers separated with a sealable interface.

The present invention is further described in connection with the drawings below. In the following figures like numbers refer to like parts throughout. Referring to FIG. 1, the sterilization apparatus comprises a first chamber 2 and a second chamber 4. The two chambers are separated by a sealable and removable interface 6 so that the two chambers can be operated independently, i.e. different items can be sterilized simultaneously in the two chambers, or one chamber is operated for sterilization while the other is not in operation. An enclosure 10 for receiving a sterilant source 12 is connected to each of chambers 4 and 2 through a valve 14a and a valve 14b, respectively. Two enclosures 10 are shown in FIG. 1. However, these two enclosures 10 can be combined into one. Enclosure 10 can be made of materials similar to those of the walls of chambers 2 and 4. The sterilant source 12 can be connected to enclosure 10 or directly to chambers 2 and 4. There are several way to control the amount of sterilant entering chamber 2 or 4 if such control is desired. For example, valves 14a and 14b can be a metering valve and the amount of sterilant flowing from enclosure 10 to chambers 2 and 4 is measured and controlled by valve 14a or 14b; or enclosure 10 is equipped with a volume reading so that the volume of the sterilant in enclosure 10 can be read; or sterilant containing wells (not shown) can be provided in the chambers to control the amount of liquid sterilant. The sterilant source 12 can be also connected directly to chambers 2 and/or 4.

Chambers 2 and 4 are equipped with a vacuum pump 16 for generating vacuum within these chambers during the sterilization process. Valve 15a and valve 15b are provided connecting vacuum pump 16 to chamber 4 and 2, respectively. They are controlled independently. Chambers 2 and 4 can also be equipped with a pump 18 to circulate sterilant between the two chambers. Chambers 2 and 4 can be of any desired shape, but a regular shape such as cylindrical or rectangular will make it easier to accommodate the interface 6.

Figure 1A:
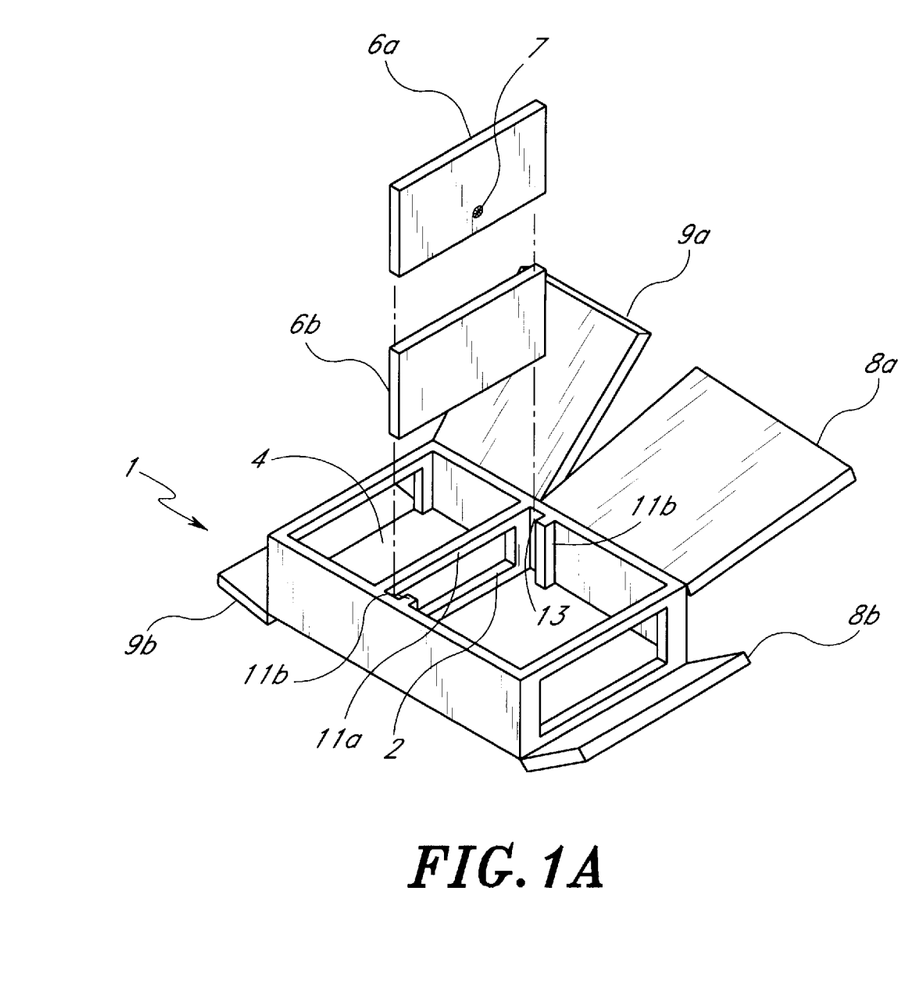
FIG. 1A is a schematic diagram of an embodiment of the apparatus of the present invention showing the interface, doors and two chambers.

FIG. 1A shows more details of chambers 2 and 4 with interface and doors. As shown in this figure, chambers 2 and 4 can be equipped with doors 8a, 8b, 9a, and 9b, respectively. One chamber does not necessarily have more than one door. There are a frame 11a and a guiding piece 11b between the two chambers. Interface 6a or 6b is secured between the two chambers through frame 11a and guiding piece 11b by sliding the interface into gap 13 defined by frame 11a and guiding piece 11b. If necessary, interface 6a or 6b can be further secured to frame 11 a by any conventional means, such as screw or clamp. A sealing O-ring (not shown) can be provided around the frame 11a to generate a good sealing between the two chambers. The interface 6a has an opening 7 adapted to receive a lumen device. Opening 7 may have different shape and size to accommodate different types of lumen devices. Under different situation, different interface can be chosen. The opening 7 is controllable. In one embodiment the opening has a shutter structure which is electrically controlled. By changing the dimension of the opening, different degree of seal between the opening and the lumen device held by the opening can be achieved.

Figure 2:
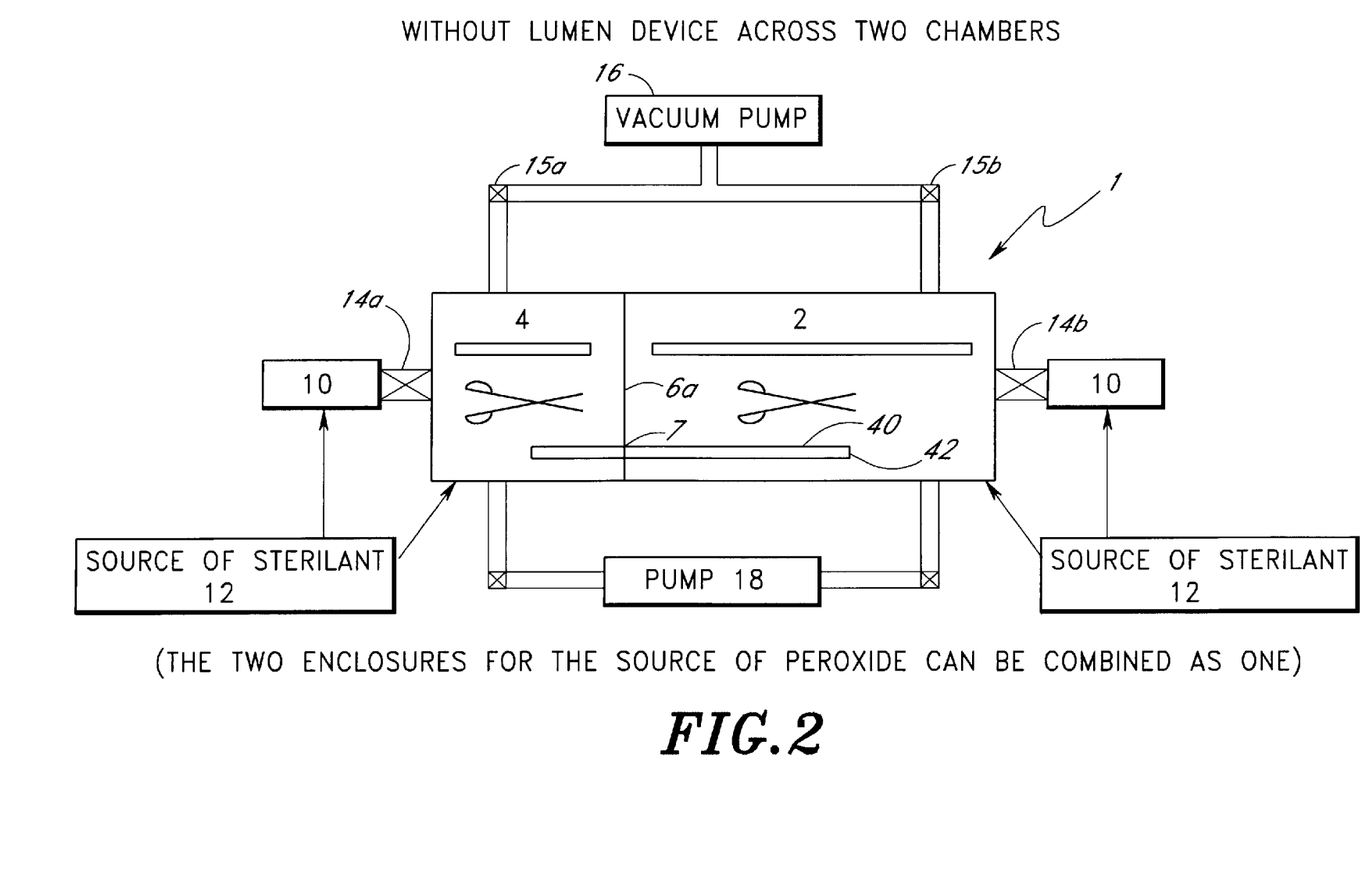
FIG. 2 is a schematic diagram of an embodiment of the apparatus of the present invention showing two chambers separated by an interface and in fluid communication through a lumen device.

FIG. 2 shows a sterilization apparatus able to generate a sterilant flow through a lumen to be sterilized. As shown in FIG. 2, the apparatus comprises a first chamber 2 and a second chamber 4. The two chambers are separated by an openable and closeable interface 6a. Interface 6a has an opening 7. A lumen device 40 with a lumen 42 is placed through the opening 7 in such a way that one end of the lumen 42 is in chamber 2 and the other end in chamber 4. At least during a part of a sterilization process for sterilizing the interior of the lumen 42, the opening 7 is gas-tight sealed around the lumen device 40 so that sterilant fluid flows through the lumen 42 under a pressure drop between the two chambers 2 and 4. Although a liquid sterilant can be used in the apparatus, sterilant vapor is preferred. The sterilant vapor can be generated with any appropriate method known to the art or with the method described in the copending application referenced previously. Generally speaking, the usual way to generate vapors in a sterilization system is the use of heating and/or vacuum. In the present invention, both heating and vacuum can be employed to generate sterilant vapor.

In order to generate a flow of sterilant fluid through the lumen 42, pressure differential has to be exist between the two ends of the lumen 42. One way of generating such a pressure gradient is to pressurize one end of the lumen 42. But it is more desirable to apply vacuum to one end of the lumen 42 with vacuum pump 16, especially when sterilant vapor is used. The two chambers can operated either under vacuum or under pressure up to about 4 atm. The temperature of the two chambers can be controlled independently through a conventional heating device (not shown). The operation temperature of the chambers are adjusted so as not to damage the device to sterilized. It is usually below 80° C., more preferably 20–55° C.

Vacuum pump 16 is used to generate vacuum in either chamber 2 or chamber 4 through valve 15b and 15a. Pump 18 is used to circulate sterilant between chamber 2 and chamber 4. If necessary, vacuum pump 16 and air pump 18 can be operated either simultaneously or sequentially.

In addition to lumen device 40, a plurality of devices can be sterilized in both chamber 2 and 4. In this embodiment, the devices to be sterilized can be retreated or not retreated with liquid sterilant. Because sterilant is circulated through the lumen 42, the interior of the lumen device 40 is mainly sterilized by the sterilant flow therethrough. This direct circulation of sterilant provides an efficient sterilization of the interior of the lumen 42, especially, when hydrogen peroxide vapor is circulated through the lumen 42. Doors can be provided for the two chambers at any convenient locations, for example, as shown in FIG. 1A. Sterilant can be provided from enclosure 10, or directly from the source of sterilant 12. The sterilant source 12 can be in the form injection, static soak, liquid flowthrough, or aerosol spray. Liquid sterilant may also be placed on the wells (not shown) on the bottom surface of the chambers and is vaporized during the sterilization by applying vacuum and/or heating.

All the features and functions of the apparatus shown in FIG. 1 and described previously are applicable to the apparatus shown in FIG. 2.

Figure 3:
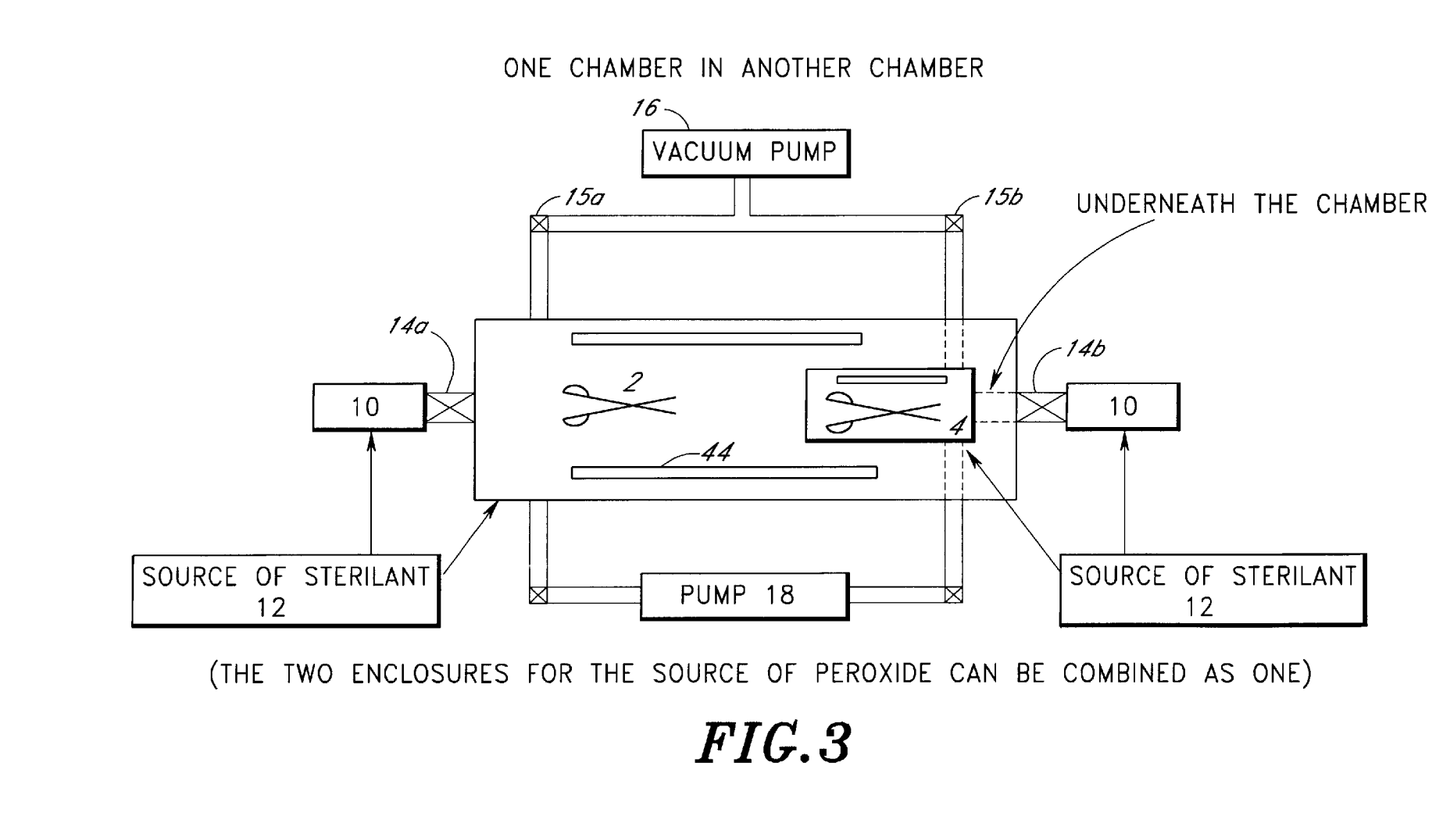
FIG. 3 is a schematic diagram of an embodiment of the apparatus of the present invention showing one chamber placed in another chamber.

FIG. 3 shows a top view of the two chambers in another embodiment of the present invention. The apparatus comprises similar elements as that shown in FIG. 2, but they are configured differently. Chamber 4 is now located inside chamber 2. Chambers 2 and 4 are still separately connected to vacuum pump 16, enclosure 10, and pump 18 as shown in FIG. 3. Pump 18 usually is not needed when there is no sterilant flow between the two chambers. The two chambers are still independently operable. One of the advantages of the arrangement is that devices with greater length such as device 44 can be accommodated in the space between chamber 2 and chamber 4.

Chambers 2 and 4 share the top surface and the bottom surface, and are equipped with two sealable doors. Chamber 2 has a large door on the top surface and chamber 4 has a smaller door on the upper surface. The smaller door is in the large door, but the two doors can be operated independently.

Figure 4:
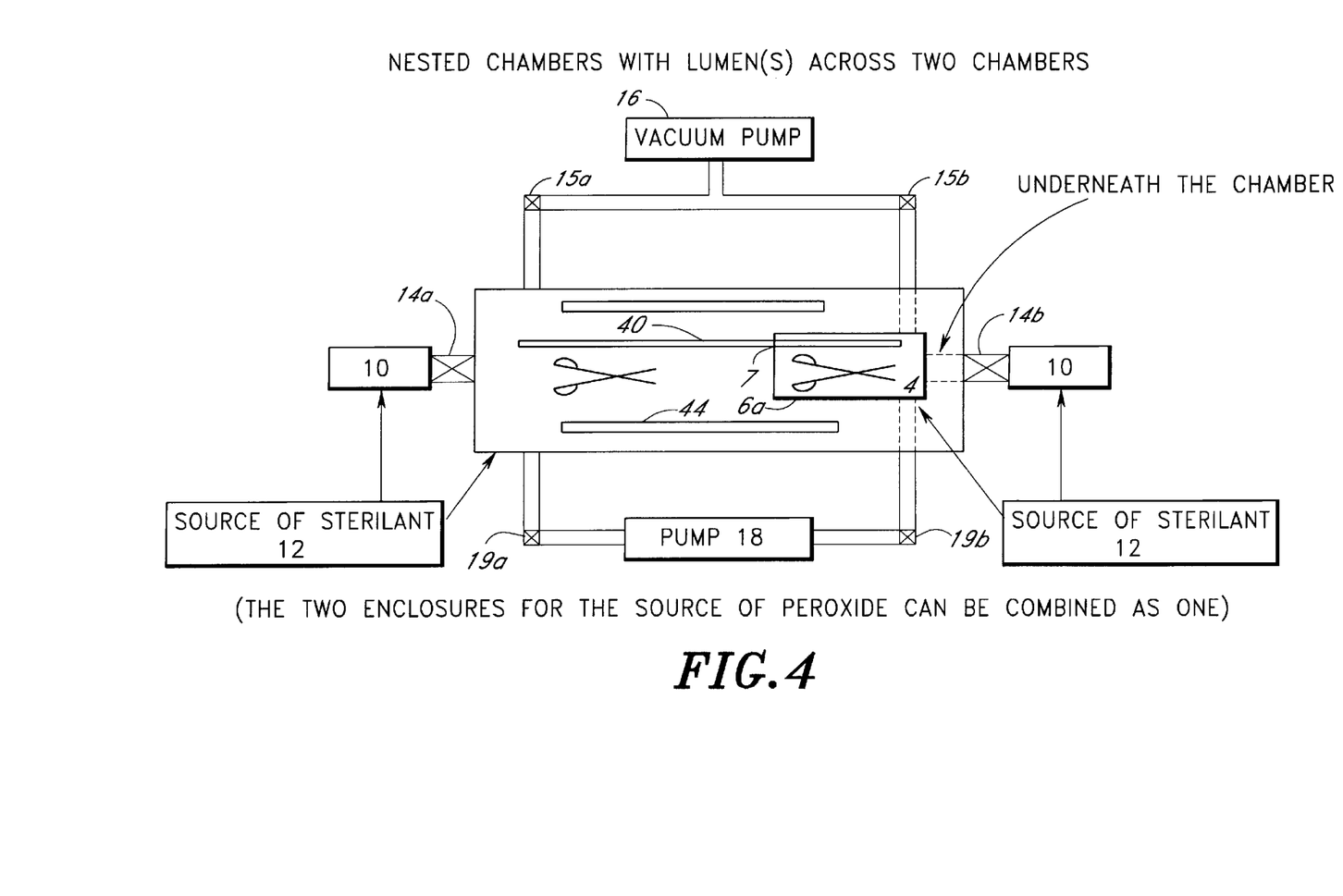
FIG. 4 is a schematic diagram of an embodiment of the apparatus of the present invention showing one chamber in another with lumen connecting the two chambers.

FIG. 4 shows an apparatus of the present invention similar to that shown in FIG. 3. The difference between the two embodiments shown in FIG. 3 and FIG. 4 is that in the apparatus of FIG. 4 chamber 2 and chamber 4 are in fluid communication through a lumen device 40. Therefore, this apparatus has all the advantages possessed by the apparatus of FIG. 3. In addition, it can be used to effectively sterilize devices with long narrow lumens. In this case, a removable interface 6a with an opening 7 is provided to accommodate the lumen device 40. The interface 6a can be installed in a similar way as discussed and shown in FIG. 1A. Valves 19a and 19b can be provided between pump 18 and the chambers.

Figure 5:
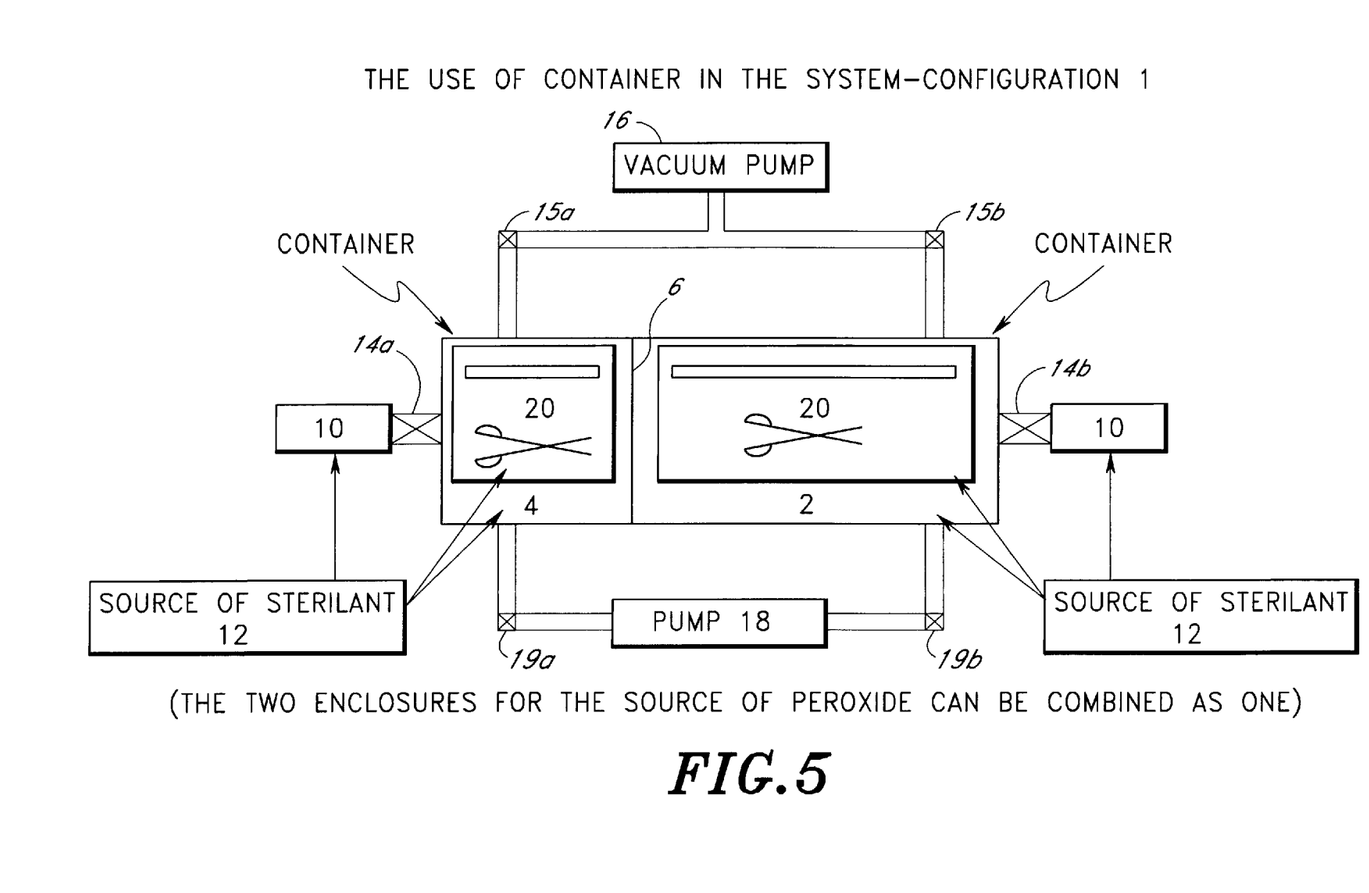
FIG. 5 is a schematic diagram of an embodiment of the apparatus of the present invention showing two chambers containing containers.

FIG. 5 demonstrates the use of a container 20 in the chambers 2 and 4. For certain devices the sterility needs to be maintained after the sterilization. A sterilant vapor-permeable and microorganism-impermeable container is usually used to achieve the goal to keep the microorganism away form the sterilized devices after the devices have been sterilized. As shown in FIG. 5, a container 20 is placed in either chamber 2 or chamber 4, or both. The rest of the system is the same as the apparatus shown in FIG. 1. The container is provided with a membrane (not shown) which is sterilant vapor-permeable and microorganism-impermeable and can be located at any convenient position on the wall of the container 20. The sterilant vapor-permeable and microorganismimpermeable membrane can be made of any conventional material known the art such as TYVEK™ nonwoven polyethylene fabric, nonwoven polypropylene such as SPUNGUARD™, or similar material. During a sterilization process, the sterilant vapor generated from a liquid sterilant in chamber 2 or 4 penetrates into the container 20 through the membrane and sterilizes the device placed inside the container 20. The devices to be sterilized can also be retreated with liquid sterilant and then the liquid sterilant contained or absorbed by the devices is vaporized under vacuum applied through vacuum pump 16. Another option is to provide the container 20 with liquid sterilant before the sterilization process starts, then close a sealable door of the container 20, and apply vacuum to the container 20 to vaporized the liquid sterilant contained in the container 20. When the sterilization cycle is complete, the container is removed form the chamber. Because of the microorganism-impermeable feature, the container 20 can maintain the sterility of the device inside the container 20. This greatly reduces the chance of re-contamination during the handling of the sterilized device.

Figure 6A:
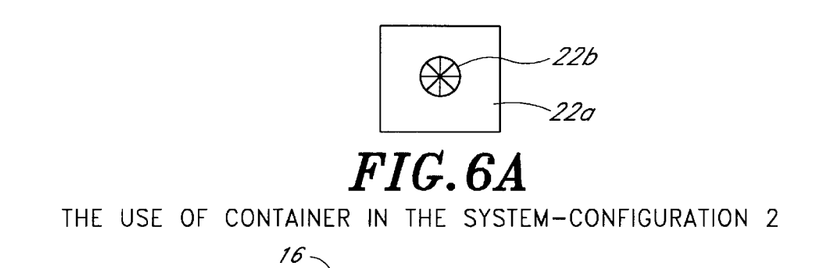
FIG. 6A is a cross sectional view of the system of FIG. 6.
Figure 6B:
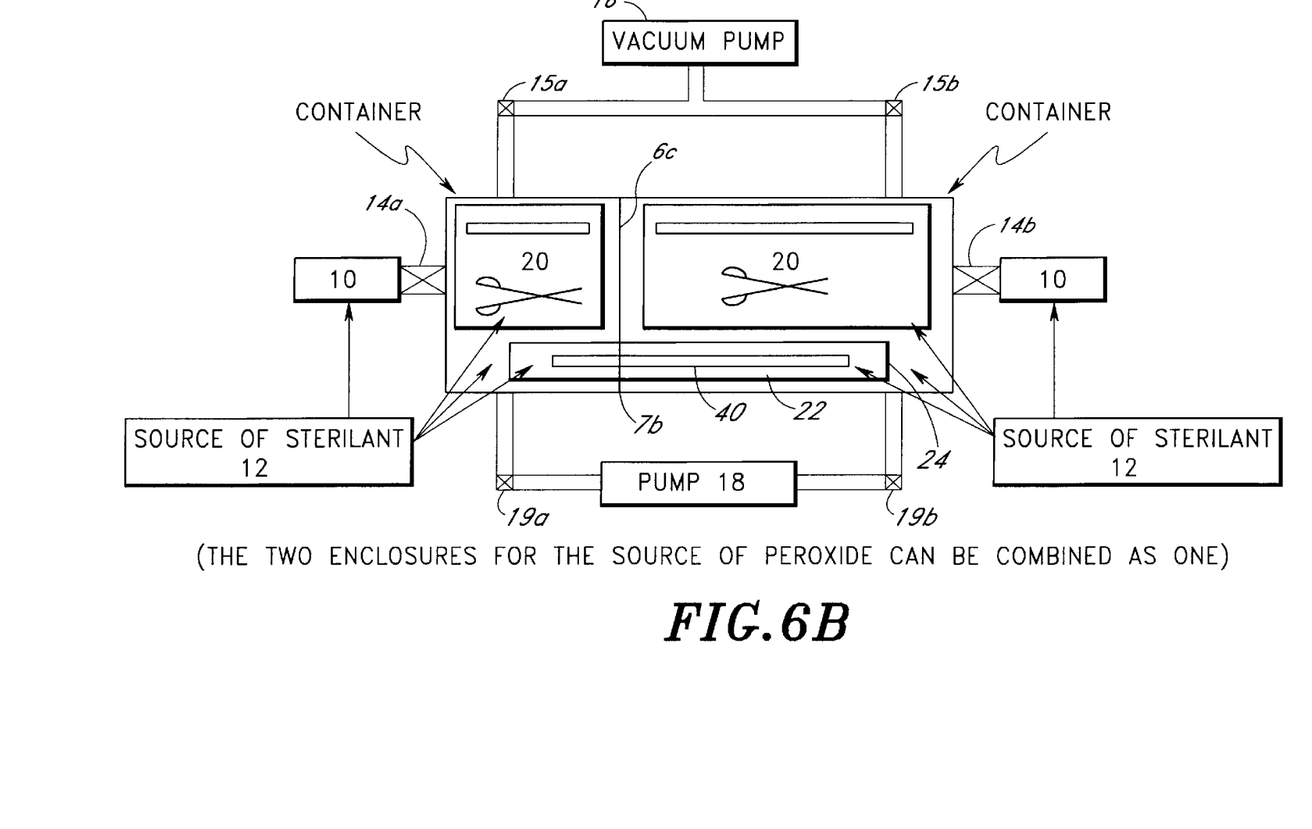
FIG. 6 is a schematic diagram of an embodiment of the apparatus of the present invention showing two chambers containing containers and being connected through a lumen.

FIG. 6 shows a sterilization apparatus similar to that of FIG. 5. In the apparatus shown in FIG. 6, a container 22 for lumen device 40 is placed across opening 7b in the interface 6c. The opening 7b is sealed around the outside of the container 22, for example, by an O-ring or other similar material mounted in the opening 7b. Container 22 also has an interface 22a with an opening 22b as shown in FIG. 6A. The opening 22b is also sealed around the outer surface of the lumen device 40 so that no gas or vapor can flow therebetween when the seal is in gas-tight seal state. When desirable, the sealing between the outer surface of the lumen device 40 and the opening 22b of the interface 22a of the container 22 can be released so that the outer surface of the lumen device 40 adjacent the sealing is sterilized. A sterilant vapor-permeable and gas-permeable, but microorganism-impermeable membrane 24 is provided to both portions of the container 22 in chamber 2 and 4. The membrane 24 can be located at any convenient position on container 22, such as at both ends of the container 22. Through membranes 24 and lumen 42 of the lumen device 40, chamber 2 and chamber 4 are placed in fluid communication. By applying vacuum to either chamber with vacuum pump 16, a pressure differential can be established and a flow of sterilant is generated between the two chambers. The container 22 serves to maintain the sterility of the lumen device 40 placed therein following the sterilization.

Figure 7:
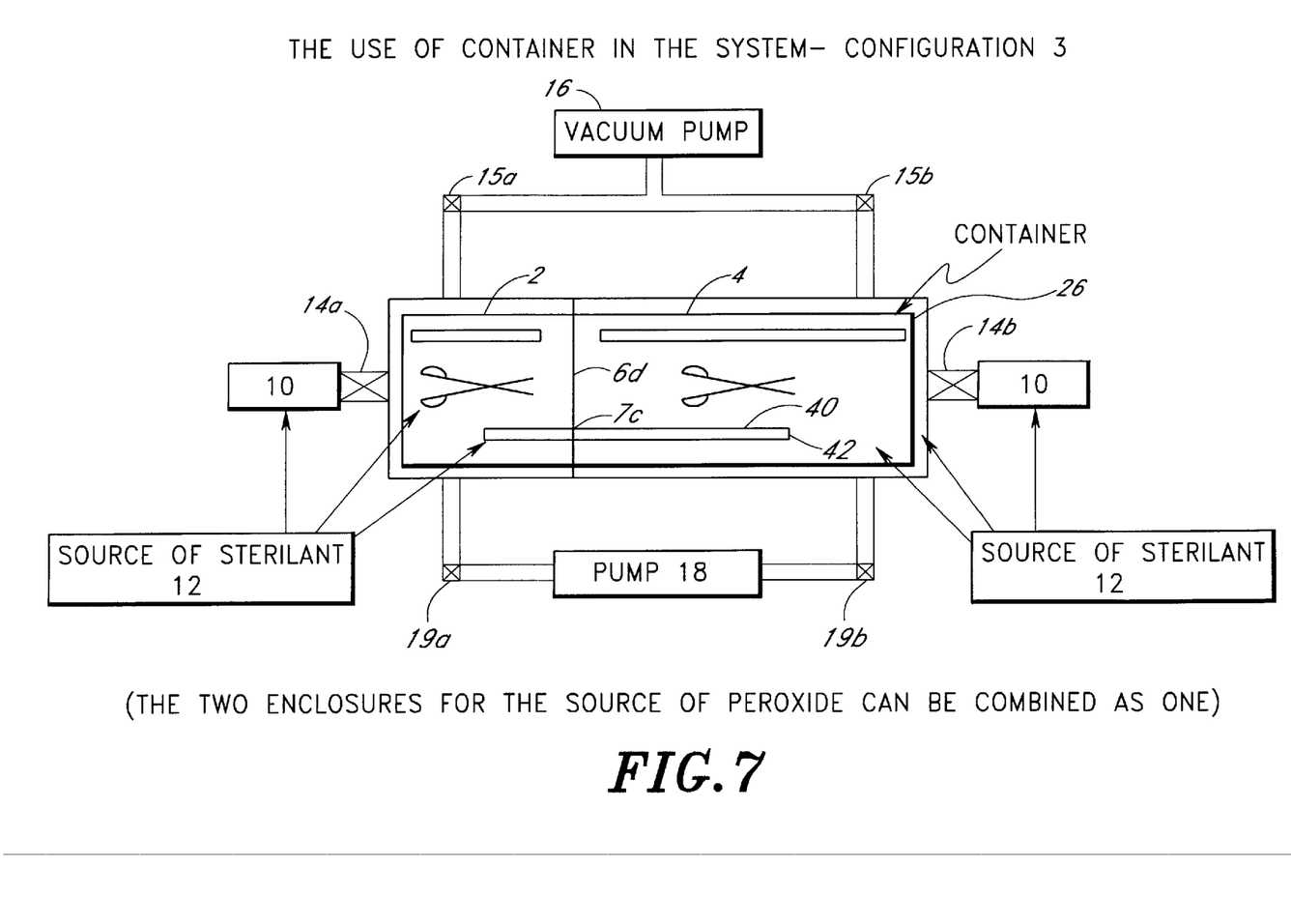
FIG. 7 is a schematic diagram of an embodiment of the apparatus of the present invention showing a container in the chambers separated with an interface.

FIG. 7 shows a sterilization apparatus which comprises a container 26. The container 26 is divided by an interface 6d. Like interface 6a described FIG. 2, interface 6d is sealable and has an opening 7c. Container 26 is accessible to sterilant source 12 or enclosure 10. The gap between the inner surface of chambers 2 and 4 and the outer surface of the container 26 is gas-tight sealed so that no air or sterilant vapor can flow through the gap form chamber 2 to chamber 4 or vice versa. In the embodiment shown in FIG. 7, the sealing of the gap between the inner surface of chambers 2 and 4 and the outer surface of the container 26 is provided at the about same location where the interface 6d separates the container 26 into two portions. The two portions of the container 26 separated by the interface 6d are in fluid communication through the lumen 42. The opening 7c is sealed around the outer surface of the lumen device 40 in the same manner as described in the section for the apparatus shown in FIG. 2. A sterilant vapor-permeable and gas-permeable, but microorganism-impermeable membrane is provided at both portions of the container 26. Thus, a pressure differential can be generated between the two chambers and between the two portions of the container 26 by means of vacuum pump 16 and/or pump 18. The pressure difference between the two portions of the container 26 forces sterilant fluid to flow through the lumen 42, and both the interior and the exterior of the lumen device 40 and other devices in the container 26 are efficiently sterilized. The sterility of the devices in the container 26 is maintained following the sterilization.

The present invention is described based on drawings and different embodiments. It is obvious to one of ordinary skill in the art that various modifications can be made without departing from the spirit and the scope of the present invention.

What is claimed is:

1. An apparatus for the sterilization of a medical device, comprising:
    a. a multi-chambered compartment having at least a first rigid chamber and a second rigid chamber therein, wherein each of said first and second chambers has a door, a pumping source, and a source of sterilant such that each of said chambers is adapted to independently serve as a sterilization chamber and can be operated independently;
    b. an openable and closeable interface between said first and second chamber; and
    c. a source of sterilant, said source adapted to provide said sterilant in said first and/or second chamber.

2. The apparatus of claim 1, further comprising a flow path between said first and second chamber, and a flow system to flow said sterilant through said flow path.

3. The apparatus of claim 2, wherein said interface has at least one opening which is openable and closeable.

4. The apparatus of claim 3, wherein said device comprises a lumen, and wherein said lumen of said device is placed through said opening such that said lumen is located partly in each of said first and second chambers.

5. The apparatus of claim 4, wherein said opening forms a gas-tight seal around said lumen.

6. The apparatus of claim 4, wherein said opening forms a loose-fitting seal around said lumen and allows sterilant to flow outside of said lumen through said opening.

7. The apparatus of claim 4, wherein said opening forms a tight-fitting seal around said lumen, said seal comprising a gas and/or liquid permeable material.

8. The apparatus of claim 3, wherein the opening in the interface is provided with an iris diaphragm.

9. The apparatus of claim 3, wherein the opening is defined by two plates with compressible material at edges or on surfaces adjacent said opening, and at least one of said plates is movable.

10. The apparatus of claim 3, wherein the opening is equipped with inflatable material so that when the inflatable material is inflated the opening is reduced to hold and seal a device to be sterilized.

11. The apparatus of claim 2, wherein said flow path is inside said multi-chambered compartment.

12. The apparatus of claim 11, wherein said flow path allows flow in both directions.

13. The apparatus of claim 12, wherein said flow path is through a lumen device.

14. The apparatus of claim 2, wherein said flow path is outside said multi-chambered compartment.

15. The apparatus of claim 14, wherein said flow path allows flow in both directions.

16. The apparatus of claim 2, wherein said flow path is a first flow path, said apparatus further comprising a second flow path.

17. The apparatus of claim 16, wherein said second flow path is outside said multi-chambered compartment.

18. The apparatus of claim 16, wherein said first flow path is in said interface.

19. The apparatus of claim 16, wherein said first flow path is inside said multi-chambered compartment and said second flow path is outside said multi-chambered compartment.

20. The apparatus of claim 2, wherein said flow system comprises a vacuum pump for applying vacuum, a pump for circulating sterilant, or heat-induced pressurization.

21. The apparatus of claim 1, wherein said interface is openable and closeable by being removable.

22. The apparatus of claim 1, wherein said interface is a removable solid plate.

23. The apparatus of claim 1, wherein said device is placed in a sterilant vapor-permeable and microorganism-impermeable container, said container maintaining the sterility of said device following sterilization and wherein said container is placed in said multi-chambered compartment.

24. The apparatus of claim 1, wherein said device is placed in either said first chamber or said second chamber.

25. The apparatus of claim 1, wherein each of said first and second chamber provides a diffusion restricted environment.

26. The apparatus of claim 1, wherein the first chamber and the second chamber have a first and a second sealable door, respectively, wherein the second sealable door is smaller than the first door and located in the first door.

27. The apparatus of claim 1, further comprising an opening without a lumen in said interface.

28. The apparatus of claim 1, wherein said source of sterilant is selected from the group consisting of an injector, a liquid flow-through device, a liquid or solid reservoir or aerosol spray device.

29. The apparatus of claim 1, wherein said source of sterilant is placed in a location selected from the group consisting of: said first chamber; said second chamber; a container wherein said container is placed in said multi-chambered compartment; an enclosure placed outside of said multi-chambered compartment, wherein said enclosure is connected to one of said first and second chambers, or to both of said first and second chamber.

30. The apparatus of claim 25, wherein said enclosure is connected to the container.

31. The apparatus of claim 25, wherein said source of sterilant is a liquid reservoir.

32. The apparatus of claim 1, wherein said sterilant comprises a liquid, a solid or condensed vapor.

33. The apparatus of claim 32, wherein said liquid comprises hydrogen peroxide or peracetic acid.

34. The apparatus of claim 32, wherein said sterilant is a solid hydrogen peroxide complex.

35. The apparatus of claim 34, wherein said hydrogen peroxide complex comprises a urea peroxide complex or sodium pyrophosphate peroxide complex or like complex.

36. The apparatus of claim 32, wherein said sterilant is a condensed vapor which comprises hydrogen peroxide or peracetic acid vapor.

37. The apparatus of claim 1, further comprising at least one additional interface.

38. The apparatus of claim 1, further comprising a heater to vaporize said sterilant.

39. The apparatus of claim 1, further comprising a plasma generator for exposing said device to a plasma.

40. The apparatus of claim 39, wherein said plasma generator is located in a separate container and said apparatus further comprises a flow system to flow said plasma into said multi-chambered compartment.

41. A method for sterilizing an interior and exterior of a lumen device, comprising:
   a. placing said device in a multi-chambered compartment having a first chamber, a second chamber, and an interface with at least one opening, such that said lumen is partly in said first chamber and partly in said second chamber across the interface;
   b. introducing a sterilant from a source of sterilant in said multi-chambered compartment; and
   c. creating directional flow of said sterilant with a pump from said first chamber, through said lumen, through said second chamber, through said pump, and back to said first chamber.

42. The method of claim 41, wherein the directional flow can be reversed.

43. The method of claim 41, wherein said pump is located outside the multi-chambered compartment.

44. The method of claim 41, wherein said opening is adjustable.

45. The method of claim 44, further comprising the step of adjusting said opening.

46. A method for sterilizing an interior and exterior of a lumen device, comprising:
   a. placing said device in a sterilant vapor-permeable and microorganism-impermeable container, said container maintaining the sterility of said device following sterilization;
   b. placing said device in said container in a multi-chambered compartment having a first chamber, a second chamber, and an interface with at least one adjustable opening, such that said lumen is partly in said first chamber and partly in said second chamber across the interface;
   c. introducing a sterilant from a source of sterilant in said multi-chambered compartment; and
   d. creating a flow of sterilant between said first chamber and said second chamber through said lumen.

47. A method for sterilizing an interior and exterior of a lumen device, comprising:
   a. placing said device in a multi-chambered compartment having a first chamber, a second chamber, and an interface with at least one adjustable opening, such that said lumen is partly in said first chamber and partly in said second chamber across the interface, wherein either or both of said first and second chambers is a diffusion restricted environment;

b. introducing a sterilant from a source of sterilant in said multi-chambered compartment; and c. creating a flow of sterilant between said first chamber and said second chamber through said lumen.

48. A method for sterilizing an interior and exterior of a lumen device, comprising:

a. placing said device in a multi-chambered compartment having a first chamber, a second chamber, and an interface with at least one adjustable opening, such that said lumen is partly in said first chamber and partly in said second chamber across the interface, wherein said opening forms a tight-fitting seal around said lumen, said seal comprising a gas and/or liquid permeable material;

b. introducing a sterilant from a source of sterilant in said multi-chambered compartment; and c. creating a flow of sterilant between said first chamber and said second chamber through said lumen.

49. A method for sterilizing an interior and exterior of a lumen device, comprising:

a. placing said device in a multi-chambered compartment having a first chamber, a second chamber, and an interface with at least one adjustable opening, such that said lumen is partly in said first chamber and partly in said second chamber across the interface;

b. warming said device to be sterilized at a pressure below atmospheric pressure;

c. introducing a sterilant from a source of sterilant in said multi-chambered compartment, wherein step (b) occurs prior to step (c); and d. creating a flow of sterilant between said first chamber and said second chamber through said lumen.

50. A method for sterilizing an interior and exterior of a lumen device, comprising:

a. placing said device in a multi-chambered compartment having a first chamber, a second chamber, and an interface with at least one adjustable opening equipped with an iris diaphragm which can seal around the device, such that said lumen is partly in said first chamber and partly in said second chamber across the interface;

b. introducing a sterilant from a source of sterilant in said multi-chambered compartment; and c. creating a flow of sterilant between said first chamber and said second chamber through said lumen.

51. A method for sterilizing an interior and exterior of a lumen device, comprising:

a. placing said device in a multi-chambered compartment having a first chamber, a second chamber, and an interface with at least one adjustable opening defined by two plates, wherein said lumen is partly said first chamber and partly in said second chamber across the interface, said plates having compressible material at edges or on surfaces adjacent said opening, wherein at least one of the plates is movable, so that the plates can be brought toward each other to hold and seal around said device;

b. introducing a sterilant from a source of sterilant in said multi-chambered compartment; and c. creating a flow of sterilant between said first chamber and said second chamber through said lumen.

52. A method for sterilizing a medical device, comprising the steps of:

a. placing said device in a sterilant vapor-permeable and microorganism-impermeable container, said container maintaining the sterility of said device following sterilization;

b. placing said device in said container in a multi-chambered compartment having a first rigid chamber, a second rigid chamber, and an adjustable interface between said first and second chambers, wherein step (a) occurs prior to step (b);

c. adjusting the interface so that a device too big to fit into the first or second chamber can be sterilized in a bigger chamber formed by said first and second chamber; and d. introducing a sterilant from a source of sterilant in said multi-chambered compartment.

* * * * *

UNITED STATES PATENT AND TRADEMARK OFFICE
CERTIFICATE OF CORRECTION

PATENT NO. : 6066294
DATED : May 23, 2000
INVENTOR(S) : Szu-Min Lin, Paul Taylor Jacobs It is certified that error appears in the above-indentified patent and that said Letters Patent is hereby corrected as shown below:

In Figure 2, the Title at the top of the Figure should read: "WITH[OUT] LUMEN DEVICE ACROSS TWO CHAMBERS".

Signed and Sealed this

Third Day of April, 2001

Attest:

NICHOLAS P. GODICI

Attesting Officer     Acting Director of the United States Patent and Trademark Office